United States Patent [19]

Szkrybalo

[11] 4,061,489

[45] Dec. 6, 1977

[54] ABSCISSION COMPOSITIONS

[75] Inventor: William Szkrybalo, Verona, N.J.

[73] Assignee: Hoffmann-La Roche Inc., Nutley, N.J.

[21] Appl. No.: 548,937

[22] Filed: Feb. 11, 1975

Related U.S. Application Data

[63] Continuation-in-part of Ser. No. 347,035, April 2, 1973, abandoned.

[51] Int. Cl.$^2$ .............................................. A01N 9/00
[52] U.S. Cl. .......................................... 71/88; 536/4
[58] Field of Search .................. 71/88, 75; 260/340.7, 260/209 R

[56] References Cited

U.S. PATENT DOCUMENTS

| | | | |
|---|---|---|---|
| 2,491,933 | 12/1949 | Ruys et al. | 260/340.7 |
| 2,547,822 | 4/1951 | Johnson, Jr. et al. | 424/357 |
| 2,589,150 | 3/1952 | Schneider | 424/357 |
| 3,776,936 | 12/1973 | Singhal et al. | 71/DIG. 1 |

FOREIGN PATENT DOCUMENTS

| | | | |
|---|---|---|---|
| 427,286 | 4/1935 | United Kingdom | 260/340.7 |

OTHER PUBLICATIONS

Kazimirova, "Cyclohexane Compounds of Monoses etc.," (1955), CA 50 p. 4898 (1956).
Reichstein et al., "Eine Ergiebige Synthese der-1-Ascorbinoaur, etc." (1934), Helv. Chim. Acta 17, pp. 311-328 (1934).
Hulyalkar et al., "Synthesis of L–Aeabinose-5-c$^{14}$" (1963), Can. J. Chem. 41, pp. 1898-1904 (1963).
BASF, "Antifoaming Agents" (1969), CA 72 No. 57023a., (1970).
Copper et al., "The Effect of Ascorbic Acid, etc.," (1967), CA. 67, No. 89938r, (1967),
Baig et al., "L-Ascorbic Acid Biosynthesis etc.," (1970), CA 74, No. 10425j, (1971).
Loewus et al., "Biosynthesis and Degradation etc.," (1970), CA 74, No. 108221g, (1971).
Tipson et al., "Infrared Absorption Spectra of Some etc.," (1959), J. of Res. of Nat. Bureau of Standards 62, pp. 257-263 & 282 (1959).

*Primary Examiner*—Glennon H. Hollrah
*Attorney, Agent, or Firm*—Samuel L. Welt; Bernard S. Leon; William M. Farley

[57] ABSTRACT

Abscission compositions containing as the active ingredients 2,3:4,6-di-O-(substituted)-2-keto-L-gulconic acids, salts and esters thereof and, preferably, 2,3:4,6-di-O-isopropylidene-2-keto-L-gulonic acid, its salts and esters are described.

15 Claims, No Drawings

ABSCISSION COMPOSITIONS

RELATED APPLICATION

This application is a continuation-in-part of U.S. patent application Ser. No. 347,035 filed Apr. 2, 1973, and now abandoned the benefit of the date of which is hereby claimed.

BACKGROUND OF THE INVENTION

The emphasis on mechanical harvesting of tree-borne fruit has stimulated extensive investigation of chemicals which facilitate harvesting of such fruit by reducing the force of attachment between the fruit and the stem. To be efficacious, such chemicals, known as abscission agents, much reduce the force required to remove the fruit from the stem, aid in separating the complete stem from the fruit leaving a clean unbroken plug, cause a minimum of burning and pitting of the tree's fruit, delay rotting of the fruit after it is either picked or falls to the ground, have no deleterious effect on green fruit and have no appreciable detrimental effect on the leaves of treated plants. The ideal abscission agent is simple, inexpensive, amenable to simple application, e.g. by spraying, and compatible with aqueous and/or oily spray compositions. In addition to those requirements for efficacy, an abscission agent must be non-toxic to humans and/or animals when eaten and must meet government safety standards as a food additive or "residue".

SUMMARY OF THE INVENTION

This invention relates to abscission compositions and methods of using them. More particularly, this invention relates to abscission compositions containing as the active abscission agent compounds represented by the formula:

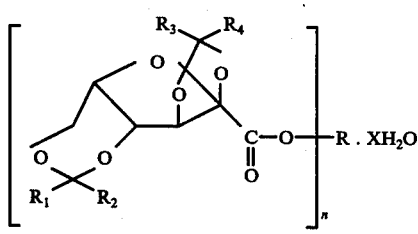

I wherein, when $n$ is 1, R is hydrogen, sodium potassium, ammonium, substituted ammonium wherein the substituents are one or more of lower alkyl, lower alkenyl or hydroxy (lower alkyl), straight or branched chain alkyl of from 1 to 20 carbon atoms, straight or branched chain alkenyl of from 1 to 20 carbon atoms, straight or branched chain alkynyl of from 1 to 20 carbon atoms, or halo-lower alkyl and, when $n$ is 2, R is calcium, magnesium or lower alkylene, $R_1$, $R_2$, $R_3$ and $R_4$ are hydrogen, straight or branched chain alkyl of from 1 to 20 carbon atoms, straight or branched chain alkenyl of from 1 to 20 carbon atoms, straight or branched chain alkynyl of from 1 to 20 carbon atoms, halo-lower alkyl, aryl or $R_1$ and $R_2$ together and $R_3$ and $R_4$ together are each a saturated ring containing from 3 to 8 carbon atoms, $n$ is a integer from 1 to 2 and X is a number from 0 to 1, enantiomers and racemic mixtures.

The compounds which are the preferred active abscission ingredients in the abscission compositions of this invention are represented by the formula

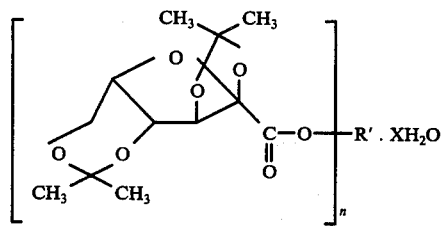

II wherein, when $n$ is 1, R' is hydrogen, sodium, potassium, ammonium, substituted ammonium wherein the substituents are one or more of lower alkyl, lower alkenyl or hydroxy (lower alkyl), straight or branched chain alkyl of from 1 to 20 carbon atoms, straight or branched chain alkenyl of from 1 to 20 carbon atoms, straight or branched chain alkynl of from 1 to 20 carbon atoms, or halo-lower alkyl and, when $n$ is 2, R' is calcium, magnesium or lower alkylene, $n$ is an integer from 1 to 2 and X is a number from 0 to 1, enantiomers and racemic mixtures.

The compounds represented by formulas I and II are all of the L configuration since they are derived from the naturally occurring ketohexose, L-sorbose. While L-sorbose is the only known naturally occurring form of sorbose, its enantiomer, D-sorbose, can be synthesized. Compounds with the D-configuration and racemic mixtures of the compounds can be made using either D-sorbose or a mixture of D- and L-sorbose in identical preparatory procedures as for the L-configuration as discussed hereinafter.

All structural formulas set forth herein are for convenience only and are not intended to depict any absolute configuration. The formulas cover enantiomers and racemic mixtures. The Examples and other description, unless specifically noted otherwise, are directed to the racemic compounds.

As used herein, the term "lower alkylene" denotes a divalent substituent consisting of straight or branched chain aliphatic hydrocarbons of from 1 to 7 carbon atoms and having its valence bonds from different carbons. The term "lower alkyl" includes both straight and branched chain saturated aliphatic groups containing from 1 to 7 carbon atoms, such as methyl, ethyl, n-propyl, isopropyl, n-butyl and the like. The term "lower alkoxy" includes straight or branched chain alkoxy groups containing from one to seven carbon atoms such as methyl, ethoxy and the like. The term "lower alkenyl" includes monovalent substituents of both straight and branched chain ethylenically unsaturated aliphatic groups containing from one to seven carbon atoms such as vinyl, allyl and the like. The term "aryl" refers to monocyclic aromatic hydrocarbon such as phenyl and phenyl radicals having one or more alkyl, alkenyl, alkynyl, alkoxy or halo-lower alkoxy substituents thereon. "Halo" includes fluorine, chlorine or bromine.

DETAILED DESCRIPTION OF THE INVENTION

It has been found that when an abscission composition containing a compound represented by Formulas I and II is applied to fruit-bearing trees or bushes the force required to remove the fruit from the stem is thereby significantly reduced in comparison to that required to remove the fruit from untreated trees. Further, fruit removed from trees with the aid of the abscission compositions of the present invention has been found to be relatively free from pitting and rotting.

The compositions of the present invention can be applied to the fruit-bearing trees in liquid or powdered formulations. Application may be made to the roots, trunks, limbs, leaves or fruit. For example, the abscission composition according to the present invention can be dusted on the trees to be absorbed by the roots. The preferred method of application, and the most efficient, is to apply the compositions in the form of an aqueous spray. If desired, an oily spray may be used. In the interest of economy, however, an aqueous spray is preferred.

In order to achieve the most efficient use of the abscission compositions of the present invention, it is preferred to apply them from about 1 to 2 weeks prior to harvesting of the fruit. This spray time is temperature dependent with the longer time period used at cooler temperatures. In areas where a rainfall is expected subsequent to application but prior to harvesting, a conventional sticking agent may be incorporated into the compositions. Typical examples of such sticking agents include glue, casein, salts of alginic acids, cellulose gums and their derivatives, polyvinyl pyrrolidone, vegetable gums, propylene glycol, invert syrup, corn syrup and the like.

Compositions of this invention contain, as the essential active abscission ingredient, a compound represented by Formulas I and II. If desired, agriculturally acceptable adjuvants used for application to trees may be utilized in conjunction with the active ingredients of the abscission compositions of the present invention. The term "agriculturally acceptable adjuvant" as used herein includes:

a. agriculturally acceptable inert carrier materials as, for example, surface active agents, carriers, sticking agents, stabilizers, fillers and the like and b. other active agricultural materials such as herbicides, fungicides, insecticides or plant growth regulants which complement the active abscission ingredient or extend the useful life of the composition.

It is understood, of course, that the adjuvant added to the abscission compositions of this invention either only the inert materials of (a), the active materials of (b) or a combination of materials from (a) and (b).

The concentration of the compounds represented by Formulas I and II suitable for use in the novel abscission compositions of the present invention vary, but, in order to be most effective, it is necessary that a sufficient amount be present to provide from about 0.05 to about 1.5% by weight of the active compound in spray solution. This amount will vary according to the fruit to be sprayed and the size of the tree or bush. The application rate is that which provides a sufficient active abscission compound to be effective in facilitating harvesting. For spray applications, the solution containing the abscission composition is applied to the tree until runoff. In commercial operations this involves the application of from 350 to 100 gallons of a dilute spray solution ( 0.1-1% by weight of active ingredient) per acre, depending upon the number and size of the trees sprayed.

In order to form the preferred aqueous spray formulations embodying the abscission compositions of the present invention, the active abscission ingredient is dispersed in a water carrier. From about 0.1 to about 0.5% by weight, based on the weight of the carrier, of a surface active agent may be inclined in the aqueous spray compositions. Typical surface active agents are Triton ® B-1956 ®, a water-dispersible, resin-based surfactant manufactured by Rohm and Haas and X-77 (Chevron-Ortho) a non-ionic type composition containing as the principal functioning agent alkylaryl-polyoxyethylene glycols, free fatty acids and isopropanol.

A wettable powder premix for preparing such aqueous solution comprises from about 40 to about 60% by weight of the active ingredient and from about 60 to about 40% by weight of a surfactant.

An especially preferred aqueous spray formulation of this invention can be prepared by dispersing in the water carrier a wettable dry powder containing, in percents by weight based on the total weight of the dry powder, about 90% of the sodium salt of 2,3:4,6-di-O-isopropylidene-2-keto-L-gulonic acid (equivalent to about 80% of the anhydrous free acid), about 6% of sodium lauryl sulfate surfactant, about 2.5% of a silica-gel anticaking agent, about 0.5% of sodium stearate antifoaming agent and about 1% of anhydrous sodium carbonate. The amount of sodium carbonate added is adjusted to provide a pH of 8-10 when the formulation is added to water.

Such a dry powder formulation readily dissolves in water to form sprayable formulations containing an amount of the active abscission ingredient which is effective in stimulating abscission.

The abscission compounds used in the compositions of this invention effectively abscind a variety of fruits from trees. Typical fruits with which these compositions are efficacious include oranges, grapefruits, olives, apples, cherries, blueberries, prunes, filberts and the like. The are also efficacious in use with other crops such as cotton (to drop the leaves) and soybeans.

As has been stated, it is preferred to apply the novel abscission compositions of the present invention to fruit trees in the form of an aqueous spray. In this respect, it is within the purview of the present invention to utilize equivalent amounts of the water soluble salts of the compounds represented by Formulas I and II. Such salts include for example the sodium salt, the potassium salt, the ammonium salt and the like.

The novel abscission compositions of this invention which contain 2,3:4,6-di-O-isopropylidene-2-keto-L-gulonic acid, known also as DAG, are buffered to a pH range of 5-7 by the addition of potassium hydrogen phosphate to the aqueous solution. Such buffering is necessary in view of the known instability of DAG in aqueous solution below pH 5. Buffering is not needed when salts of DAG are used.

In those cases where the compounds to be used are not soluble in water, emulsifiable concentrates or wettable powder formulations of the active ingredients are prepared which can be dissolved in water to form the spray solutions.

DAG may be prepared as an emulsion concentrate using N-methyl-2-pyrrolidone or nitropyrrolidone according to the following formulations:

|  | % by weight of Total Composition |
|---|---|
| DAG | 50 |
| Atlox 2081B* | 4 |
| N-methyl-2-pyrrolidone or | 46 |

-continued

|  | % by weight of Total Composition |
|---|---|
| Nitropyrrolidone |  |

*Atlox 2081B is a blend of polyoxyethylene sorbitan esters of fatty and resin acids and alkyl aryl sulfonate. (Atlas Powder)

The DAG esters are formulated as xylene-based emulsifiable concentrates for mixing with water. Emulsions are prepared from these concentrates which contain from 25 to 50% by weight of the active ingredient. Typical emulsifiable concentrates for the DAG esters are listed below.

|  | % by weight of Total Composition | |
|---|---|---|
| Active Ingredient | 25 | 50 |
| Xylene | 71 | 46 |
| Atlox 3403[1] | 2 | — |
| Atlox 3404[2] | 2 | — |
| Emulphor EL 620[3] | — | 2 |
| Drewmulse GMC-8[4] | — | 2 |

[1]Atlox 3403 is a blend of polyoxethylene ethers, polyoxyethylene glyceride and an alkyl aryl sulfonate. (Atlas Powder)
[2]Atlox 3404 is a blend of polyoxyethylene alkyl aryl ether and an alkyl aryl sulfonate. (Atlas Powder)
[3]Emulphor EL 620 is a polyethylated vegetable oil. (GAF Corp.)
[4]Drewmulse GMC-8 is a monoglyceride of low molecular weight saturated coconut fatty acid. (E.F. Drew & Co.)

Wettable powders are prepared using an inert diluent, e.g., kaolin or silicagel. A typical wettable dry powder for use in spray solutions would contain, in percents by weight based on the weight of the composition, from about 1 to about 5% of an inert diluent, from about 3 to about 10% of a surfactant such as Triton B-1956, X-77 and sodium lauryl sulfate, from about 0.1 to about 1% of an anti-foaming agent such as sodium stearate, from about 0.4 to about 1.5% of a buffer to maintin the pH of the formulation in water at 8–10 and, the balance, the active abscission agent.

Since oranges can be considered a typical fruit representative of those amenable to treatment by chemical abscission agents, the efficacy of the novel abscission compositions of the present invention may be illustrated with respect thereto.

The sodium salt of 2,3:4,5-di-O-isopropylidene-2-keto-L-gulonic acid was tested for its activity as an abscission agent for citrus fruits, i.e., oranges. Aqueous solutions containing 0.05, 0.1, 0.25, 0.5 and 1.0% by weight of the sodium salt and 0.5% of Triton B-1956 were prepared. These solutions were applied as a spray of velencia orange, marsh seedless grapefruit and ruby red grapefruit trees. One week after spray application, the only observable effect was a slight leaf drop on trees treated as the higher application rates. Two weeks after spraying most of the oranges and grapefruits on trees sprayed at the 1.0% rate had dropped. Trees sprayed at the 0.5% rate had dropped about half their fruit and the remaining fruit was very loose.

In addition to the abscission effect, the fruit also showed a marked enhancement in color, i.e., a much deeper and darker color than the untreated fruit.

The sugar content and/or total solids in the treated fruits also increased in comparison to the untreated fruit.

Similar results have been obtained using sprays, for example, the ammonium or diethanol ammonium salts or the n-butyl ester of 2,3:4,6-di-O-isopropylidene-2-keto-L-gulonic acid, the sodium salt of 2,3-0-isopropylidene-4,6-O-benzylidene-2-keto-L-gulonic acid and the sodium salt of 2,3-O-iso-propylidene-4,6-O-ethylidene-2-keto-L-gulonic acid.

Similar abscission activity has been demonstrated on blueberries, prunes and filberts using aqueous spray solutions of the sodium salt of 2,3:4,6-di-O-isopropylidene-2-keto-L-gulonic acid containing from about 2500 to about 5000 ppm of the 2,3:4,6-di-O-isopropylidene-2-keto-L-gulonic acid equivalent.

2,3:4,6-di-O-isopropylidene-2-keto-L-gulonic acid monohydrate is a well-known chemical of commerce and is an intermediate in the formation of L-ascorbic acid. It is prepared by the oxidation in alkaline or neutral media of diacetone-L-sorbofuranose which is, in turn prepared from the reaction of L-sorbose with acetone in the presence of a strong acid.

Salts of DAG are prepared by conventional processes. DAG is added with rapid stirring to an aqueous solution of a base at room temperature. The solution is monitored to maintain pH above 7. Upon completion of the reaction, excess water is removed under high vacuum. Anhydrous acetone is then added to the resulting syrup (about 10 volumes) with overnight stirring. The white crystalline precipitate which forms is filtered, washed with acetone and dried. In the case of the non-volatile bases, equivalent amounts of acid are admixed. For the volatile bases, e.g. $NH_4OH$ and $(CH_3)_2NH$, excess base is added and the excess is subsequently removed in the vacuum evaporation.

Since DAG is not stable under normal esterification conditions such as the Fischer esterification procedure, the novel esters of DAG are prepared by reaction with the appropriate lower alkyl, lower alkenyl or lower alkinyl halide under basic conditions at room temperature using an inert organic solvent such as dimethyl formamide (DMF). The esters are insoluble in water but soluble in methanol, acetone, ethanol chloroform, pentane, benzene, ether and the like.

Compounds in which the 4,6-O-isopropylidene group has been replaced are prepared by a ketal interchange reaction in which DAG is dissolved in the desired ketone, aldehyde, ketal or acetal using an acid catalyst.

Representative of the ketones and aldehydes which can be used in the preparatory procedure are those of the general formula

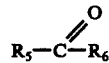

wherein $R_5$ can be, e.g., methyl, ethyl, lower alkyl, phenyl or p-methoxyphenyl and $R_6$ can be, e.g. methyl, ethyl, lower alkyl or hydrogen. Typical compounds include diethyl ketone, methyl ethyl ketone, paraldehyde, benzaldehyde, and p-methoxyaldehyde. Ketones in which both R groups are large are not satisfactory due to possible steric hindrance effects. Where an unsymmetrical aldehyde or ketone is used, the larger or bulkier group occupies the "exo" position ($R_1$ of Formula I) to form a new asymmetric center.

Any strong acid can be used as the catalyst with perchloric acid the preferred catalyst. Other representative acids include sulfuric acid, hydrochloric acid, p-toluene sulfonic acid, methane sulfonic acid and trifluoromethane sulfonic acid.

A temperature range of from about −20° to about 50° C. can be used with a range of 20°–30° C. (room temperature) preferred. 100° C., near the decomposition point of DAG, is the limiting temperature.

The compounds in which both O-isopropylidene groups have been replaced are prepared from L-sorbose following the procedure described in Reischstein and Grussner, *Helv. Chim. Acta,* 17, 311 (1934). In brief, a suitable ketone or aldehyde is reacted with L-sorbose in the presence of a strong acid catalyst e.g., sulfuric acid, at room temperature or below. The intermediate which forms, 2,3:4,6-di-O-alkylidene-α-L-sorbofuranose, is subsequently oxidized in alkaline or neutral media.

In the preparation of the di-O-alkylidene sorbofuranose, the strong acid catalysts include sulfuric acid, perchloric acid, hydrochloric acid, p-toluene acid and the like with sulfuric acid preferred.

Since the reaction is exothermic room temperature or below are used with the preferred temperature range being from about 0° C. to about −20° C.

In the subsequent preparation of the acid from the sorbofuranose intermediate, oxidation is carried out in alkaline or neutral media using such agents as $NaMnO_4$, $K_2Cr_2O_7$, $KMnO_4/KOH$ and $NaOCl/Ni^{2+}$ with the latter two preferred. In addition, the oxidation can also be achieved catalytically using palladium or platinum and oxygen.

A temperature range of from room temperature to 100° C. can be used with a range from about 50° to about 60° C. preferred.

2,3:4,6-di-O-methylene-2-keto-L-gulonic acid was prepared as described below following the procedure in the aforesaid *Helv. Chim. Acta* publication. A solution of 30 grams of sulfuric acid in 35 grams of water were added to a mixture of 50 grams of trioxane and 10 grams of L-sorbose. The resulting solution was heated to 80° C. and then cooled on an ice bath. 250 ml. of a saturated solution of potassium carbonate was added and a salt separated. The salt was filtered and washed with potassium carbonate and chloroform. These washings were added to the filtrate which was then extracted four times with chloroform. The chloroform extracts were dried over sodium sulfate to yield 4.8 grams of a yellow syrup which after vacuum distillation at 0.1 mm and 130°–135° C., yielded a solid. This solid was recrystallized from benzene to yield 1.5 grams of white crystals of 2,3:4,6-di-O-methylene-α-L-sorbofuranose.

This material was heated at 50°–60° C. for 4 hours with 1.2 grams of potassium hydroxide and 0.8 grams of potassium permanganate in 25 ml. of water. An additional 0.8 grams of potassium permanganate were added and the reaction was stirred without heating overnight. The mixture was extracted with cold methylene chloride which was evaporated to a residue. The residue was taken up in toluene, filtered and allowed to crystallize to yield 2,3:4,6-di-O-methylene-2-keto-L-gulonic acid, m.p. 124°–125° C.

By analogous procedure using ketones and aldehydes of the general formula

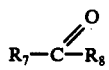

wherein $R_7$ can be halo-lower alkyl and $R_8$ can be halo-lower alkyl or hydrogen, active compounds in which $R_1$ and $R_2$ or $R_1$, $R_2$, $R_3$ and $R_4$ of Formula I are halo-lower alkyl can be prepared.

The following Examples illustrate the invention.

EXAMPLE 1

A 0.5% aqueous solution of the sodium salt of 2,3:4,6-di-O-isopropylidene-2-keto-L-gulonic acid is prepared by dissolving 0.417 pounds of the active ingredient and 0.417 pounds of B-1956 surfactant in 10 gallons of water. This solution is suitable for field use as a spray for, e.g., orange trees.

EXAMPLE 2

An emulsifiable concentrate of n-butyl 2,3:4,6-di-O-isopropylidene-2-keto-L-gulonate was prepared by admixing 0.417 pounds of the active ingredient, 1.184 pounds of xylene, 0.033 pounds of Atlox 3403 and 0.033 pounds of Altox 3404, 1.67 pounds of this mixture will firm with 10 gallons of water a sprayable aqueous emulsion containing 0.5% of the n-butyl ester.

EXAMPLE 3

A dry formulation was prepared by admixing the following ingredients, in percents by weight based on the total weight of the composition:

| Ingredient | % |
|---|---|
| Sodium salt of 2,3-di-O isopropylidene-2-keto-L-gulonic acid | 90.0 |
| Duponol ME Dry[1] | 6.0 |
| Sodium stearate (antifoaming agent | 0.5 |
| Aerosil R-972[2] | 2.5 |
| Sodium carbonate, anhydrous | 1.0 |

[1]Duponol ME Dry (DuPont) is sodium lauryl sulfate.
[2]Aerosil R-972 (Degussa) is a silicagel anticaking agent.

This formulation corresponds to one having an aqueous acid equivalent of 80%, 2,3:4,6-di-O-isopropylidene-2-keto-L-gulonic acid.

This formulation is added to water to form solutions (~1%) which are suitable for field use as a spray for, e.g., prune trees.

EXAMPLE 4

The abscission activity of 2,3:4,6-di-O-isopropylidine-2-keto-L-gulonic acid (DAG) was evaluated on almond trees.

Single tree plots of full-grown, Texas Mission variety almond trees, about 4.5 meters high, were used for the evaluation.

Aqueous spray solutions of the sodium salt of DAG were prepared containing from 5,000 to 10,000 ppm of DAG acid equivalent.

The sprays were applied to the trees with a hydraulic spray until run-off, i.e., approximately 400–600 gallons per acre.

Twenty-eight days after spray application, the abscission effect was evaluated. The trees were struck three times with a heavy stick and the percent nut drop was determined from the ratio of the number of nuts on the ground to the number of nuts remaining on the branches. Results are tabulated below.

Table 1

| Effect of DAG on the Abscission of Almond Nuts | | |
|---|---|---|
| Treatment | DAG Spray Concentration, ppm | % Nut Drop |
| Control | — | 5 |
| DAG, sodium salt | 5,000 | 30 |
| Control | — | 45 |
| DAG, sodium salt | 10,000 | 85 |

The data indicate that a significant abscission effect was achieved.

EXAMPLE 5

The abscission activity of 2,3:4,6-di-O-isopropylidene-2-keto-L-gulonic acid (DAG) was evaluated on blueberries, prunes and filberts (hazel nuts).

For the blueberry evaluation, bushes of the Blue Ray variety, 1.5 m. tall and established 10 years were used with single bush treatments replicated four times.

Eight-year old established prune trees, Parsons variety, were used for the prune evaluation in a single branch unreplicated test.

Fifteen-year old established hazel nut trees, Bacelona variety, were used for the filbert evaluation in a single branch unreplicated test.

Aqueous spray solutions, containing from 1,000 to 5,000 ppm of DAG acid equivalent and 0.5% (volume/volume) of "Tronic" surfactants, were prepared using the sodium salt of DAG. These solutions were applied as foliar sprays to the blueberry bushes and to branches of the prune and hazel nut trees. Application was by a Hudson hand sprayer operated at 30 psi. Spray was continued until run-off, i.e., 120 gallons per acre for blueberry bushes and 400 gallons per acre for the prune and hazel nut trees.

The abscission effect was evaluated on the blueberry bushes after 21 days by noting if berries fell to the ground when the bushes were hit sharply with a stick.

The abscission effects on the prune and hazel nut trees were evaluated after 14 and 31 days, respectively. In these cases, the treated branches were shaken and the number of prunes or nuts which fell were recorded.

Results are tabulated below.

TABLE II

Abscission Effect of Sodium 2,3:4,6-di-isopropylidene-2-keto-L-gulonic acid

A. Blueberries

| Spray Treatment | DAG, Spray Concentration,ppm | Observations |
| --- | --- | --- |
| Control | — | No abscission |
| DAG, sodium salt | 1,000 | No abscission |
| DAG, sodium salt | 2,500 | Abscission |
| DAG, sodium salt | 5,000 | Abscission |
| DAG, sodium salt | 10,000 | Abscission |

B. Prunes

| Spray Treatment | DAG, Spray Concentration,ppm | No. of Prunes Dropped on Shaking |
| --- | --- | --- |
| Control | — | 7 |
| DAG, sodium salt | 1,000 | 7 |
| DAG, sodium salt | 2,500 | 12 |
| DAG, sodium salt | 3,300 | 19 |
| DAG, sodium salt | 5,000 | 17 |

C. Filberts

| Spray Treatment | DAG, Spray Concentration,ppm | No. of Hazle Nuts Dropped on Shaking |
| --- | --- | --- |
| DAG, sodium salt | 1,000 | 21 |
| DAG, sodium salt | 2,500 | 92 |
| DAG, sodium salt | 3,300 | 68 |
| DAG, sodium salt | 5,000 | 53 |
| Control | — | 20 |
| Control | — | 35 |
| Control | — | 22 |
| Control | — | 19 |

The data indicate that DAG is efficacious as an abscission agent for blueberries, prunes and hazel nuts.

EXAMPLE 6

This Example demonstrates that 2,3:4,6-di-O-isopropylidene-2-keto-L-gulonic acid, its salts and esters and various derivatives thereof are not converted by plants to ascorbic acid, a known abscission agent.

2,3:4,6-di-O-isopropylidene-2-keto-L-gulonic acid (DAG) was labeled with carbon 14 at the 6 position of the furanoid ring. The specific activity was 7.2 $\mu$ Ci/mg. A labeled methyl 2,3:4,6-di-O-isopropylidene-2-keto-L-gulonate (DAG, methyl ester) was prepared by esterification of the labeled DAG in an etheral diazomethane solution. The specific activity was 6.9 $\mu$ Ci/mg.

Purity of both materials was ascertained by Thin Layer Chromatography.

For plant application, 10 mg. of active ingredient are added to 5 ml. of a 0.06 M sodium phosphate buffer solution containing 0.2% Tween 20 surfactant to form a solution with a pH of 7.0.

Wheat plants (Svenno) were raised in soil pots (5 plants per pot) and in nutrient water cultures (5 plants per beaker of a nutrient solution containing $Ca(NO_3)_2$, $KH_2PO_4$, $MgSO_4$, $KNO_3$ and traces of salts of microelements necessary for plant development.

The wheat plants used for the experiments were 2–3 weeks old and the main shoots had 4–5 leaves.

Tomato plants (Rheinland Ruhm) were raised in nutrient water cultures (2 plants per beaker). The plants used for the experiments were about 20 cm. high.

The compositions containing an active ingredient were applied to these greenhouse-raised wheat and tomato plants as 1 $\mu$ l droplets from a microsyringe. For the wheat plants, the droplets were applied to the middle zone of the second or third leaf (about 15 cm from the leaf tip). Each plant received about 47 droplets corresponding to 94 $\mu$ g of active ingredient. For tomato plants, the droplets were applied to three leaves just below the growing zone.

One set of wheat plants were sprayed, prior to application of the labeled DAG, with an unlabeled 2,3:4,6-di-O-isopropylidene-2-keto-L-gulonic acid—at a normal application rate of 4 kilograms per hectare. This was done to ascertain whether DAG undergoes different absorption, translocation and exudation effects when applied at normal rates.

All plants were grown in Therma Clima chambers under long day conditions (16 hours of light and 8 hours of dark) at a day temperature of 22° C., a night temperature of 20° C. and a relative humidity of 70%.

At specified time intervals, the plants were harvested and separated into roots and plants. The roots from the nutrient water cultures were washed under running tapwater while the roots from soil cultures were separated from the soil and air dried with the remaining soil particles removed by hand.

Plants from the nutrient water cultures were worked up as a whole. Plants from the soil cultures were separated into treated leaves, leaves above the treated leaf, leaves below the treated leaf, tillers and stems. The same parts of the replicates in one pot were combined and weighed. The plant parts were cut into small pieces and homogenized with ice cooled acetonitrile. The roots from the soil cultures were treated similarly.

Roots from the plants raised in the nutrient water culture were homogenized acetonitrile with enough dry ice added to just start the freezing of the solvent. The homogenates were then quantitatively transferred into centrifuge tubes, centrifuged and the supernatants were carefully pipetted off.

The solvent extracts of the roots were evaporated to dryness on a Rotovap, quantitatively redissolved and transferred into a small test tube with 3 ml of methanol.

The plant material extracts were partitioned with 50 ml of n-hexane. All the radioactivity stayed in the acetonitrile layer. The acetonitrile fractions were evaporated to dryness on a Rotovap and then quantitatively redissolved and transferred with 3 ml of methanol into a small test tube. Radioactivity of 20–50 μl aliquots of the methanol solutions was determined in a Packard Tricarb Model 3375 under standard conditions.

Three pots with five plants each were assayed 1, 3, 7 and 9 days after application of labeled DAG alone, 4 and 6 days after application of DAG plus labeled DAG and 1 day after application of labeled DAG, methyl ester.

The nutrient water cultures were assayed to determine whether and to what extent the active ingredient was exuded through the plant roots. Both wheat and tomato plants were assayed. The cultures were concentrated on the Rotovap and made up to a volume of 100 ml in a volumetric flask. 0.5 ml aliquots were assayed for radioactivity in the Packard Tricab.

The results, showing the absorption and translocation of the activity through the plants and exudation through the roots, are tabulated below.

| Active Ingredient | Days After Treatment | % Activity in Various Wheat Plant Parts | | | | | | | |
|---|---|---|---|---|---|---|---|---|---|
| | | Treated Leaf | | Leaf Below | Leaf Above | Tillers | Stem | Root | Total Recovered |
| | | Wash Off | Homogenate | | | | | | |
| Labeled DAG | 1 | 7.5 | 55.3 | 0.6 | 1.9 | 3.8 | 10.3 | 5.6 | 85.0 |
| Labeled DAG | 3 | 4.3 | 27.0 | 0.6 | 3.9 | 12.3 | 14.0 | 7.4 | 69.5 |
| Labeled DAG | 7 | 6.3 | 19.5 | 0.2 | 8.3 | 11.0 | 10.0 | 8.1 | 63.4 |
| Labeled DAG | 9 | 8.9 | 14.8 | 0.2 | 9.6 | 10.8 | 8.1 | 5.4 | 57.8 |
| Labeled DAG + 4 kg/ha DAG | 4 | 11.5 | 23.2 | 2.5 | 5.2 | 6.0 | 10.1 | 6.1 | 64.6 |
| Labeled DAG + 4 kg/ha DAG | 6 | 2.1 | 23.8 | 0.7 | 3.6 | 7.3 | 9.4 | 5.2 | 52.1 |
| Labeled DAG, methyl ester | 1 | 6.7 | 38.5 | 0.8 | 0.5 | 1.2 | 3.4 | 2.3 | 53.4 |

Exudation of Radioactivity After Treatment of Leaves of Wheat and Tomato Plants grown in Nutrient Solutions

| Day After Treatment | % Activity | | | | | |
|---|---|---|---|---|---|---|
| | Wheat | | | Tomato | | |
| | Plant | Root | Nutrient Solution | Plant | Root | Nutrient Solution |
| 1 | 91.4 | 6.9 | 1.8 | — | — | — |
| 2 | 86.7 | 8.8 | 4.6 | — | — | — |
| 3 | 90.1 | 2.8 | 7.2 | — | — | — |
| 7 | — | — | — | 69.6 | 7.1 | 23.6 |
| 9 | 74.5 | 4.1 | 21.3 | — | — | — |
| 13 | 63.2 | 4.8 | 32.0 | — | — | — |
| 18 | — | — | — | 65.3 | 2.7 | 30.0 |
| 24 | — | — | — | 52.5 | 2.9 | 42.6 |

The extractable radioactivity components were then analyzed by Thin Layer Chromatography (TLC) to determine the actual ingredients which migrate and are exuded.

Silica gel $F_{254}$ (0.25 mm layer, Merck) was used for the TLC plates. Replicates of plant or root extracts were combined and concentrated under a stream of nitrogen. The radioactivity fractions in the nutrient culture solutions were extracted at pH 2 with 3X 80 ml of chloroform. All extracts were dried over sodium sulfate, evaporated on a Rotovap and redissolved in 3 ml of methanol. To determine the degree of extraction recovery, an aliquot was taken for radioassay. The other aliquots were analyzed by TLC. On all TLC plates, standards of DAG and the monoacetonide of DAG, 2,3-mono-isopropylidene-2-keto-L-gulonic acid, were also chromatographed. The following solvent systems were used (expressed as parts by volume):

I chloroform-methanol-acetic acid/95:25:2
II chloroform-ethyl acetate/1:1 (for DAG, methyl ester)
III chloroform-methanol-water-acetic acid/60:44:15:2
IV pyridine-ethyl acetate-acetic acid-water/21:62:6:3

The extracts were spotted as 2 cm wide bands on the plates and after developing were scanned for radioactivity with a Berthode TLC scanner equipped with an integrator, thus allowing quantitative determination of the various peaks.

In the plant extracts, the following metabolites, identified by an M followed by a number, listed in decreasing polarity, were detected A. M1-2,3-monoisopropylidene-2-keto-L-gulonic acid
B. M2-traces
C. 2,3:4,6-di-O-isopropylidene-2-keto-L-gulonic acid
D. M3-poorly separated from DAG
E. M4
F. M5-minor, may be an artifact.

While the metabolites for M2, M3, M4 and M5 were not positively identified, none corresponded to a peak for ascorbic acid.

I claim:

1. An abscission composition comprising inert carrier material, and as an active abscission ingredient, an amount effective for abscission of a compound of the formula

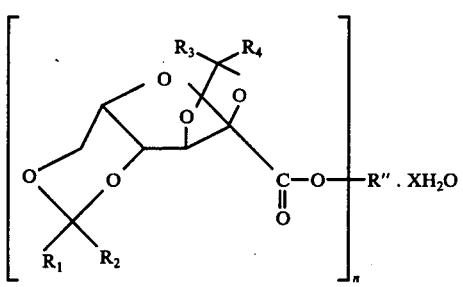

wherein, when $n$ is 1, R" is hydrogen, sodium, potassium, ammonium, substituted ammonium wherein the substitutents are one or more of lower alkyl, lower alkenyl or hydroxy (lower alkyl), straight or branched chain alkyl of from 1 to 20 carbon atoms, straight or branched chain alkenyl of from 2 to 20 carbon atoms, straight or branched chain alkynyl of from 2 to 20 carbon atoms, or halo-lower alkyl and, when $n$ is 2, R" is calcium or lower alkylene;

$R_1$, $R_2$, $R_3$ and $R_4$ are hydrogen, straight or branched chain alkyl of from 1 to 20 carbon atoms, straight or branched chain alkenyl of from 2 to 20 carbon atoms, straight or branched chain alkynyl of from 2 to 20 carbon atoms, halo-lower alkyl, phenyl or phenyl residue having one or more lower alkyl, lower alkenyl, lower alkynyl, lower alkoxy or halo-loweralkoxy substituents thereon or $R_1$ and $R_2$ together and $R_3$ and $R_4$ together are each a saturated ring containing from 3 to 8 carbon atoms; $n$ is an integer from 1 to 2 and X is a number from 0 to 1; enantiomers and racemates.

2. An abscission composition as in claim 1 wherein the active abscission ingredient comprises an amount effective for abscission of a compound of the formula

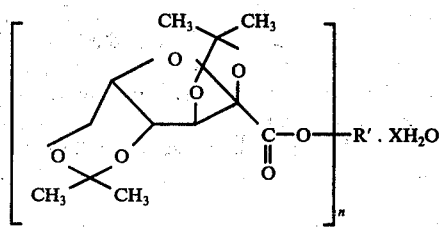

wherein, when $n$ is 1, R' is hydrogen, sodium, potassium ammonium, substituted ammonium wherein the substitutents are one or more of lower alkyl, lower alkenyl or hydroxy (lower alkyl), straight or branched chain alkyl of from 1 to 20 carbon atoms, straight or branched chain alkenyl of from 2 to 20 carbon atoms, straight or branched alkynyl of from 2 to 20 carbon atoms or halo-lower alkyl and when, $n$ is 2, R' is calcium, magnesium or lower alkylene, $n$ is an integer from 1 to 2 and X is a number from 0 to 1, enantiomers and racemic mixtures.

3. An abscission composition in accordance with claim 2 wherein the abscission compound is 2,3:4,6-di-O-isopropylidene-2-keto-L-gulonic acid monohydrate.

4. An abscission composition in accordance with claim 2 wherein the abscission compound is methyl 2,3:4,6-di-O-isopropylidene-2-keto-L-gulonate.

5. An abscission composition in accordance with claim 2 wherein the abscission compound is sodium 2,3:4,6-di-O-isopropylidene-2-keto-L-gulonate.

6. A wettable dry powder composition comprising, in percents by weight based on the total weight of the dry powder, from about 3 to about 10% of a surfactant, from about 1 to about 5% of an anti-caking compound, from about 0.1 to about 1% of an anti-foaming agent, from about 0.4 to about 1.5% of a buffer and from about 82.5 to about 94.5% of a compound of the formula

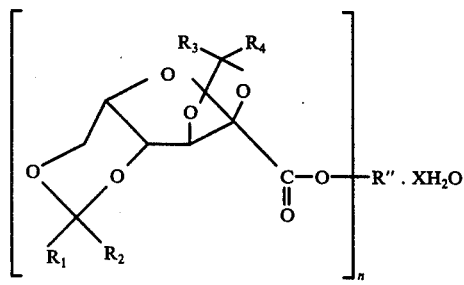

wherein, when $n$ is 1, R" is hydrogen, sodium, potassium, ammonium, substituted ammonium wherein the substitutents are one or more of lower alkyl, lower alkenyl or hydroxy (lower alkyl), straight or branched chain alkyl of from 1 to 20 carbon atoms, straight or branched chain alkenyl of from 2 to 20 carbon atoms, straight or branched chain alkynyl of from 2 to 20 carbon atoms, or halo-lower alkyl and, when $n$ is 2, R" is calcium or lower alkylene; $R_1$, $R_2$, $R_3$ and $R_4$ are hydrogen, straight or branched chain alkyl of from 1 to 20 carbon atoms, straight or branched chain alkenyl of from 2 to 20 carbon atoms, straight or branched chain alkynyl of from 2 to 20 carbon atoms, halo-lower alkyl, aryl or $R_1$ and $R_2$ together and $R_3$ and $R_4$ together are each a saturated ring containing from 3 to 8 carbon atoms; $n$ is an integer from 1 to 2 and X is a number from 0 to 1; enantiomers and racemates.

7. A wettable dry powder composition as in claim 6 wherein the active ingredient is

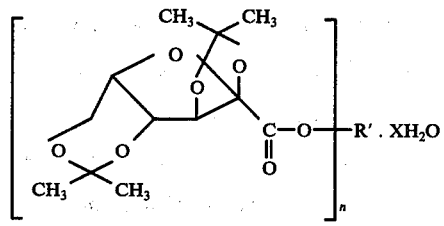

wherein when $n$ is 1, R' is hydrogen, sodium, potassium ammonium, substituted ammonium wherein the substitutents are one or more of lower alkyl, lower alkenyl or hydroxy (lower alkyl), straight or branched chain alkyl of from 1 to 20 carbon atoms, straight or branched chain alkenyl of from 2 to 20 carbon atoms, straight or branched alkynyl of from 2 to 20 carbon atoms or halo-lower alkyl and when, $n$ is 2, R' is calcium, magnesium or lower alkylene, $n$ is an integer from 1 to 2 and X is a number from 0 to 1, enantiomers and racemic mixtures.

8. A sprayable aqueous solution for stimulating abscission in fruit bearing trees and bushes which comprises, as the active ingredient, an amount effective for abscission of the dry powder composition of claim 6.

9. A sprayable aqueous solution for stimulating abscission in fruit bearing trees and bushes which comprises, as the active ingredient, an amount effective for abscission of the dry powder composition of claim 7.

10. A sprayable aqueous solution for stimulating abscission in fruit-bearing trees and bushes which comprises, in percents by weight based on the weight of the solution, as the active ingredient, from about 0.05 to about 1.5% of a compound of the formula

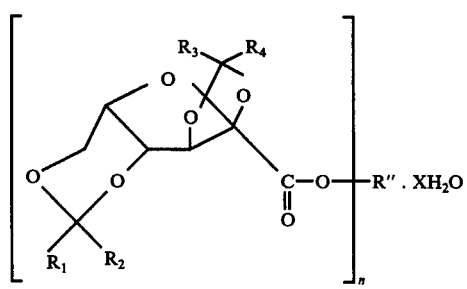

wherein, when $n$ is 1, R" is hydrogen, sodium, potassium, ammonium, substituted ammonium wherein the substitutents are one or more of lower alkyl, lower alkenyl or hydroxy (lower alkyl), straight or branched chain alkyl of from 1 to 20 carbon atoms, straight or branched chain alkenyl of from 2 to 20 carbon atoms, straight or branched chain alkynyl of from 2 to 20 carbon atoms, or halo-lower alkyl and, when $n$ is 2, R" is calcium or lower alkylene; $R_1$, $R_2$, $R_3$ and $R_4$ are hydrogen, straight or branched chain alkyl of from 1 to 20 carbon atoms, straight or branched chain alkenyl of from 2 to 20 carbon atoms, straight or branched chain alkynyl of from 2 to 20 carbon atoms, halo-lower alkyl, aryl or $R_1$ and $R_2$ together and $R_3$ and $R_4$ together are each a saturated ring containing from 3 to 8 carbon atoms; $n$ is an integer from 1 to 2 and X is a number from 0 to 1; enantiomers and racemates and from about 0.1 to about 0.5% of a surface-active agent.

11. A sprayable aqueous solution for stimulating abscission in fruit-bearing trees and bushes which comprises, in percents by weight based on the weight of the solution, as the active ingredient, from about 0.05 to about 1.5% of a compound of the formula

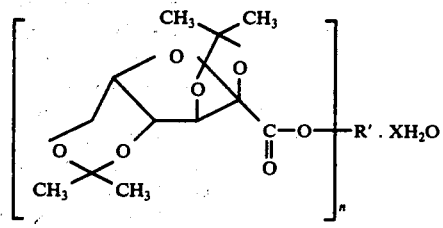

wherein, where $n$ is 1, R' is hydrogen, sodium, potassium ammonium, substituted ammonium wherein the substitutents are one or more of lower alkyl, lower alkenyl or hydroxy (lower alkyl), straight or branched chain alkyl of from 1 to 20 carbon atoms, straight or branched chain alkenyl of from 2 to 20 carbon atoms, straight or branched alkynyl of from 2 to 20 carbon atoms or halo-lower alkyl and when, $n$ is 2, R' is calcium, magnesium or lower alkylene, $n$ is an integer from 1 to 2 and X is a number of from 0 to 1, enantiomers and racemic mixtures. and from about 0.1 to about 0.5% of a surface-active agent.

12. A method of reducing the force required to abscind fruit from fruit trees which comprises applying to said trees an effective amount of the composition in claim 1.

13. A method of reducing the force required to abscind fruit from fruit trees which comprises applying to said trees an amount effective for abscission of the composition of claim 2.

14. A method of reducing the force required to abscind fruit from fruit trees which comprises applying to the trees the sprayable aqueous solutions of claim 8.

15. A method of reducing the force required to abscind fruit from fruit trees which comprises applying to the trees the sprayable aqueous solution of claim 9.

* * * * *